(12) United States Patent
Klausz

(10) Patent No.: US 8,335,294 B2
(45) Date of Patent: Dec. 18, 2012

(54) MEDICAL IMAGING SYSTEM WITH ANTI-DIFFUSION GRID

(75) Inventor: Remy Klausz, Neuilly sur Seine (FR)

(73) Assignee: General Electric Company, Schenectady, NY (US)

( * ) Notice: Subject to any disclaimer, the term of this patent is extended or adjusted under 35 U.S.C. 154(b) by 200 days.

(21) Appl. No.: 12/832,314

(22) Filed: Jul. 8, 2010

(65) Prior Publication Data

US 2011/0033029 A1 Feb. 10, 2011

(30) Foreign Application Priority Data

Jul. 20, 2009 (FR) ...................................... 09 55030

(51) Int. Cl.
*G01N 23/04* (2006.01)
(52) U.S. Cl. .......................................... 378/62; 378/155
(58) Field of Classification Search ..................... 378/62, 378/154, 155
See application file for complete search history.

(56) References Cited

U.S. PATENT DOCUMENTS

| | | | |
|---|---|---|---|
| 4,542,521 A | 9/1985 | Hahn | |
| 6,850,597 B2 * | 2/2005 | Matsumoto et al. | 378/154 |
| 7,327,826 B2 | 2/2008 | Hanke | |
| 2003/0095636 A1 | 5/2003 | Ogura | |
| 2007/0133750 A1 | 6/2007 | Graumann | |

FOREIGN PATENT DOCUMENTS

GB 1101892 1/1968

* cited by examiner

*Primary Examiner* — Hoon Song
(74) *Attorney, Agent, or Firm* — Global Patent Operation

(57) ABSTRACT

The invention relates to a process for acquisition of one or more radiological image(s) of an object of a region of interest on a patient, obtained by means of a radiological imaging system, in which the system includes: a radiation source, a detector arranged opposite the source and at least one anti-diffusion grid, which process includes steps consisting of: determining characteristics of the object to be imaged; controlling, according to the characteristics determined, a movement of the anti-diffusion grid in order to position it in or remove it from an operational position between the object and the detector, in which the operational position corresponds to a position of the grid centered on the source-detector axis and parallel to the plane including the detector; and acquiring images of the structure exposed to the radiation emitted by the source.

8 Claims, 3 Drawing Sheets

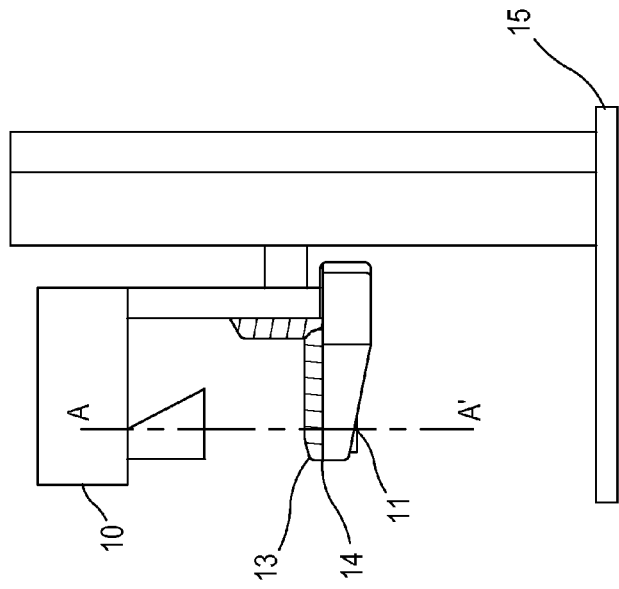
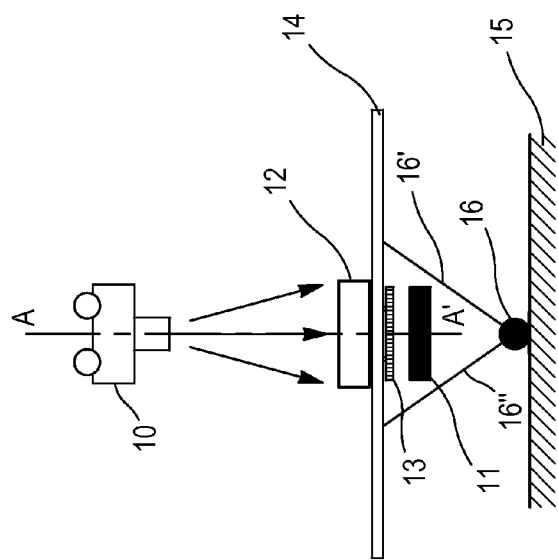
FIG. 1
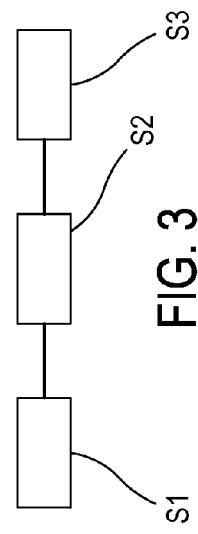
FIG. 3

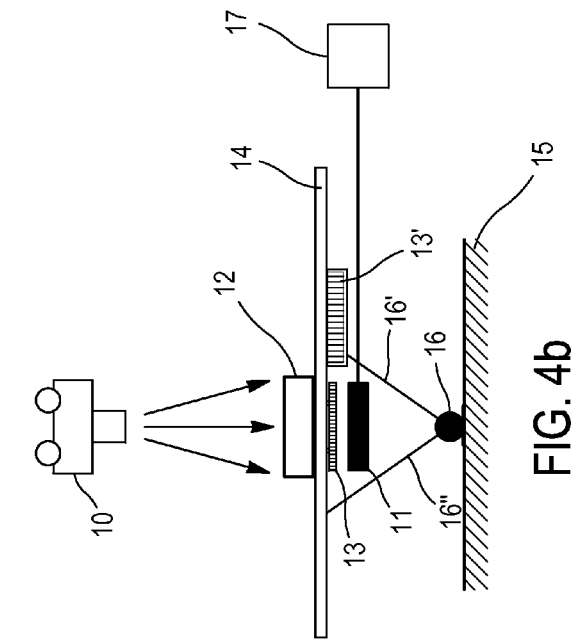
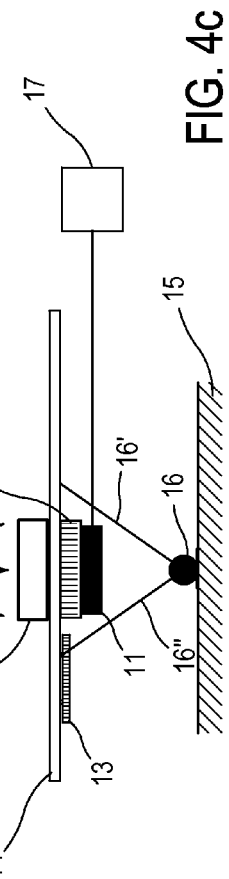
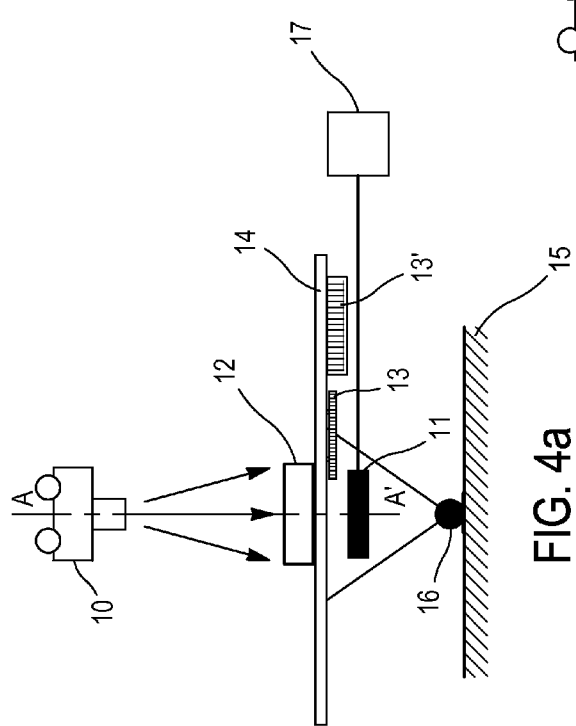
FIG. 4a
FIG. 4b
FIG. 4c

MEDICAL IMAGING SYSTEM WITH ANTI-DIFFUSION GRID

CROSS-REFERENCE TO RELATED APPLICATIONS

This application claims priority under 35 U.S.C. §119(a)-(d) or (f) to prior-filed, co-pending French patent application number 0955030, filed on Jul. 20, 2009, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

The invention relates to imaging.

More particularly it concerns a process for acquisition of one or more radiological image(s) obtained by means of a radiological imaging system, and relates more specifically to those implementing an anti-diffusion grid.

2. Description of Related Art

As shown in FIG. 1, a radiological imaging apparatus includes an X-ray source 10 and an image receptor 11, between which an object of which an image is to be taken is positioned. It is noted that the object can be an anatomical structure, for example a breast in the case of a mammography examination. More generally, it is an object 12 located in a region of interest on a patient.

The source 10 transmits a radiation beam of which the intensity is attenuated as it passes through the object 12, partially by absorption and partially by diffusion in the object. The image receptor 11 is sensitive to the intensity of the radiation.

The presence of the diffused radiation leads to degradation of the contrast of the image obtained and to a reduction in the signal-to-noise ratio, which is particularly disruptive, when details of the object are to be displayed 12.

More specifically, the presence of the diffused radiation leads to degradation of the contrast-to-noise ratio of the image of details of the object.

To overcome this problem, it is known to provide an anti-diffusion grid 13 between the object 12 and the image receptor 11. This grid 13 is positioned in a plane parallel to the plane including the receptor 11, which will hereinafter be called the "grid positioning plane".

Such a grid is particularly indicated in the case of mammography examinations. In the context of these examinations, a very high detection sensitivity is indeed desired.

FIG. 2 shows a mammography apparatus including an anti-diffusion grid 13.

As known per se, there are cases in which the presence of the grid provides no advantage, i.e. in situations in which the degradation caused by the presence of the grid is no longer compensated for by the advantages procured by its presence, i.e. the rejection of a significant amount of the radiation diffused. This is particularly true when the radiation diffused by the object is significantly lower than the radiation transmitted by the object (in particular when, in mammography, the ratio varies between $\frac{1}{4}$ and 1).

Such situations are encountered in the following cases: structure with a low thickness and structure placed at a certain distance between the receptor and the source if it is desirable, for example, to image the structure in detail.

Thus, according to the situations encountered, it would be suitable to remove the grid on the basis of the observations and expertise of the operator.

However, this presents the disadvantage of complicating and slowing the examination procedure, since a manual intervention is necessary. Indeed, it is desirable to limit examination times.

Consequently, there is a need to be capable of simply and automatically controlling the use or non-use of an anti-diffusion grid during a radiological examination.

BRIEF SUMMARY OF THE INVENTION

The invention enables the positioning of an anti-diffusion grid to be controlled in a radiological imaging system without intervention from outside the system.

Thus, a first aspect of the invention relates to a process for acquisition of a radiological image of an object of a region of interest on a patient, obtained by means of a radiological imaging system, in which the system includes: a radiation source, a detector arranged opposite the source and at least one anti-diffusion grid.

The process of the invention includes steps consisting of determining the characteristics of the object to be imaged, controlling, according to the determined characteristics, a movement of the anti-diffusion grid in order to position it in or remove it from an operational position between the object and the detector, in which the operational position corresponds to a position of the grid centered on the source-detector axis and parallel to the plane including the detector, and acquiring images of the structure exposed to the radiation emitted from the source.

An advantage of controlling the grid according to parameters of the object to be imaged is that the presence or absence of the grid enables the need to increase the resulting intensity of the radiation emitted by the source to be limited. Indeed, in the presence of the grid, the intensity of the radiation must be increased in order to compensate for the attenuation in the radiation that it produces. Consequently, if the grid is not necessary in consideration of the object to be imaged, the dose of radiation on the patient can be reduced.

Other aspects of the process of the invention are the following:

the determination of characteristics of the object consists of estimating the radiologically equivalent thickness of the object to be imaged and/or estimating the mechanical thickness of the object to be imaged;

the determination of the characteristics of the object to be imaged consists of determining the weight or the body mass of the patient.

According to a second aspect, the invention relates to a radiological imaging system including: a radiation source, a detector arranged opposite the source and at least one anti-diffusion grid.

The system according to the invention is characterized in that it also includes: means for determining characteristics of the object to be imaged, means for controlling, according to the determined characteristics, a movement of the anti-diffusion grid in order to position it in or remove it from an operational position between the object and the detector, in which the operational position corresponds to a position of the grid centered on the source-detector axis and parallel to the plane including the detector.

According to a third aspect, the invention relates to a product computer program comprising program code instructions for executing the process according to the first aspect of the invention.

BRIEF DESCRIPTION OF THE DRAWINGS

Other features and advantages of the invention will become clearer from the following description, which is provided for purely illustrative and non-limiting purposes and must be read in reference to the appended drawings, in which, aside from FIGS. 1 and 2 discussed above:

FIG. 3 shows a block diagram of the steps of the process according to the invention;

FIGS. 4a, 4b and 4c respectively show a radiological imaging system according to different positions of the grid controlled by the process of the invention.

DETAILED DESCRIPTION OF THE INVENTION

Figure 5:
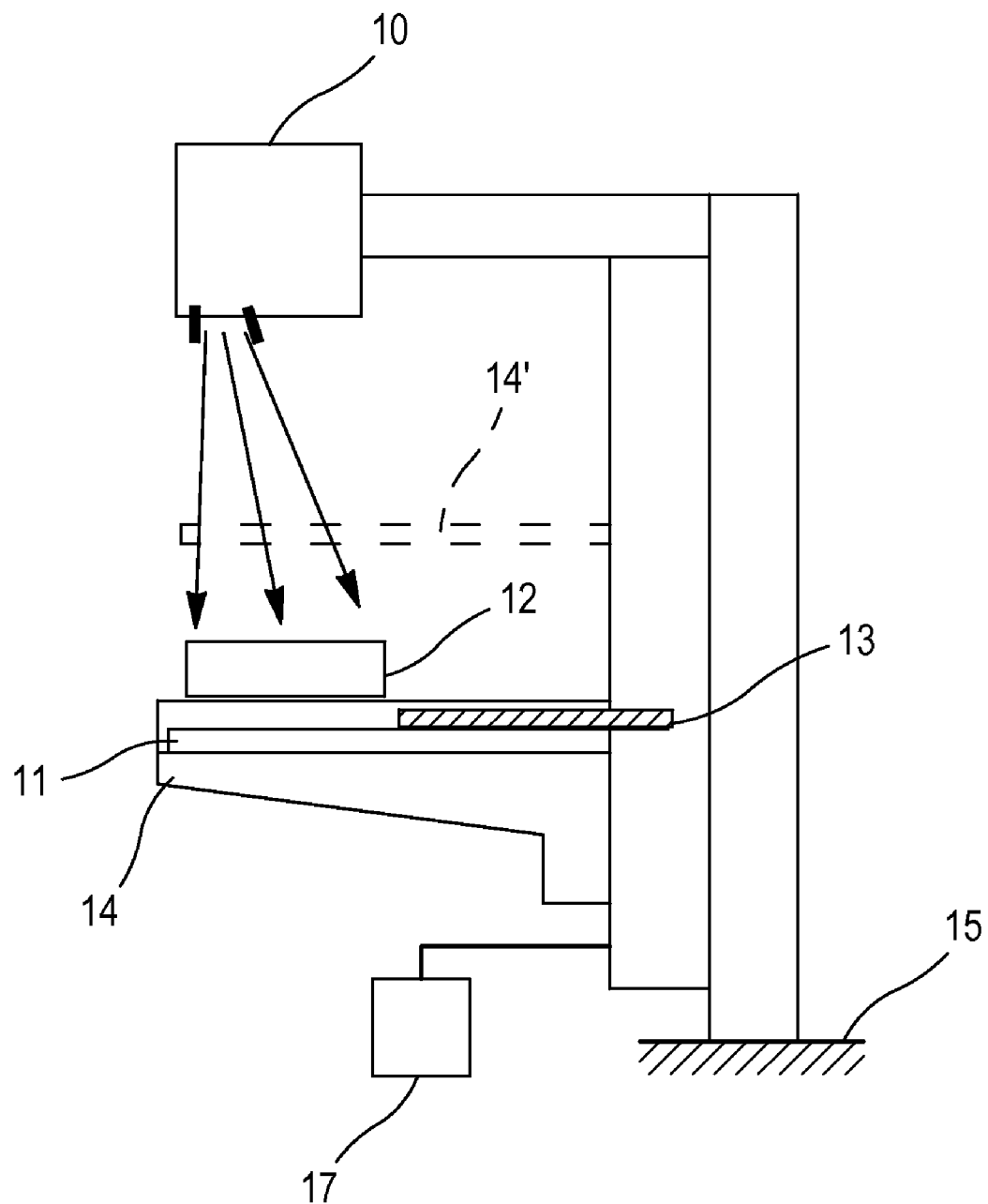
FIG. 5 shows a mammography apparatus implementing the process according to the invention.

A process for acquisition of radiological images obtained by means of a radiological imaging system is described below.

As indicated above, such a system includes a radiation source 10, a detector 11 arranged opposite the source and at least one anti-diffusion grid 13.

Such a medical imaging system is intended to obtain images of an object 12 that is positioned between the source 10 and the detector 11.

First, in a step S1, the object 12 to be imaged is characterized.

Such a characterization enables it to be determined automatically, according to characteristics of the object thus obtained, whether or not it is advantageous to place the anti-diffusion grid between the radiographed object 12 and the detector 11, then, according to this determination, to move 12 the grid 13 so as to bring it, as necessary, to its "operational" position.

It is specified here that by "operational" position, we mean a position of the grid centered on the source-detector axis (AA') and parallel to the plane including the detector.

The movement of the grid is performed without intervention by the operator.

The presence or absence of the anti-diffusion grid is dependent at least on the object 12 to be imaged.

Finally, the image acquisition S3 is performed.

The control S2 of the movement of the grid from its operational position or to its operational position is dependent at least on the characteristics of the object to be imaged.

The determination of the characteristics of the object can consist of estimating the thickness $e_s$ of the object to be imaged; for example, in the case of a mammography examination, the thickness of a compressed breast. In this case, the breast is compressed between the support 14 and a compression plate 14' (or paddle) (see FIG. 5).

According to the thickness $e_s$, the movement of the grid from its operational position or to its operational position is controlled S2 so that the acquisition S3 of radiological images is performed in the presence or in the absence of the grid.

The presence of the grid is considered to be necessary when the determined thickness $e_s$ is greater than 5 cm (on this topic, see the article of Boone published in the journal Medical Physics, October 2000, page 2408). It should nevertheless be noted that this limit value can change, in particular, according to the properties of the grid. In general, by using the concept of the improvement factor of the contrast-to-noise ratio as defined by Gennaro et al. in the article in the journal Medical Physics, February 2007, volume 34, issue 2, pages 547-555, it is considered that the grid is used when this factor is greater than 1, and that the presence of the grid is not advantageous when this same ratio is less than 1.

The thickness of the breast can be estimated by using the position of the compression plate 14' (see FIG. 5) or dedicated measurement devices using mechanical-optical methods, or other methods.

A second possibility consists of using pre-exposure process that enable—as known—the radiological configuration necessary for the acquisition of radiological images to be determined.

During the pre-exposure, the radiologically equivalent thickness $e_q$ of the structure is estimated. To obtain explanations of the radiologically equivalent thickness, reference can be made to document EP 0 402 244.

Thus, according to the object 12 to be imaged, the need to position the grid or not can be determined during the acquisition process. In addition, it is also possible to use predetermined parameters, obtained for example in a previous examination. In particular, a mammary thickness obtained in such a previous examination can be used.

The movement of the grid can be controlled according to the equivalent thickness $e_q$, the thickness $e_s$ of the structure, or the composition of the structure. Each of these characteristics can be considered alone or in combination.

It is noted that the pre-exposure can be performed with or without the anti-diffusion grid, according, for example to the thickness $e_s$.

Alternatively, during pre-exposure, an estimation of the amplitude of the residual diffused radiation can be obtained by placing, between the source and the object to be imaged, a transparent plate with opaque pellets. For technical information on these transparent plates, reference can be made to document U.S. Pat. No. 4,677,681.

Another implementation of the process according to the invention relates to its use in general radiology. FIGS. 4a, 4b and 4c show a table used to perform a radiological examination.

In the case of such a use, a stationary grid or a vibrating grid is used.

Below, a second embodiment in which two grids are used separately or together is described.

In FIG. 4a, there is no grid placed between the source 10 and the detector 11. In FIG. 4b, a first type of grid is placed between the object to be radiographed 12 and the detector 11, while in FIG. 4c another type if grid is provided.

In this type of equipment, the grids are advantageously placed below the table forming the support 14.

To move the grids, control means 17 enable the retraction of the grid to be controlled. These means are of a known type, such as: motor, feedback control or means of the same type as those used to position a cassette door in front of a radioscopic image receptor.

The choice of features of each of the two grids that can be used is made in order to best correct for the radiation diffused, corresponding to two categories of patients that may be placed on the support 14, and characterized, for example, by their body mass.

A grid with radio-opaque elements having a thickness of between 12 and 35 µm is used when the patient has an average body mass.

A grid with radio-opaque elements having a thickness of between 50 and 70 µm is used when the patient has a large body mass (i.e. the patient is obese).

It is specified that, by patient of average body mass, we mean a patient with a Body Mass Index (BMI) of between 18.5 and 24.9 kg/m$^2$, and, by obese patient, we mean a patient with a BMI above 30.

In the case of a radiological system as shown in FIGS. 4a, 4b and 4c, the object 12 is positioned on a support 14 pivoting around a connection 16, in which the structure is connected by a structure 16', 16" to said connection 16. The connection 16 is attached to the ground 15 so that the assembly formed by the support 14, the detector 11 and the object 12 can pivot around the connection 16. The grid 13 is arranged below the support 14 including means (not shown) that enable the grid to be moved.

The process described above is, for example, stored in storage means 17 connected to the imaging system.

Similarly, in the case of a mammography system as shown in FIG. 5, the grid is also arranged below the support 14, enabling, in this case, in particular a breast to be supported.

In an embodiment, aside from the characteristics of the object to be imaged, the movement of the grid can also be determined by the radiological configuration necessary for the acquisition, which is determined during the pre-exposure (for explanations on pre-exposure, reference can be made to document EP 0 402 244 and/or document EP 0 465 360).

What is claimed is:

1. A method of acquiring one or more radiological images of a region of interest of an object, obtained by a radiological imaging system, wherein the system comprises a radiation source, a detector arranged opposite the radiation source and at least one anti-diffusion grid, the method comprising:
    determining characteristics of the object to be imaged, wherein the determined characteristics of the object to be imaged are indicative of an expected amount of radiation diffused by the object to be imaged relative to an expected amount of radiation diffused by such objects generally;
    controlling, according to the determined characteristics of the object to be imaged, a movement of the at least one anti-diffusion grid in order to position the at least one of the plurality of anti-diffusion grids in or to remove the at least one of the plurality of anti-diffusion grids from an operational position between the object and the detector, wherein the operational position corresponds to a position of the grid centered on the source-detector axis and parallel to a plane including the detector; and
    acquiring images of the object exposed to the radiation emitted by the source.

2. The method according to claim 1, wherein determining the characteristics of the object comprises estimating a radiologically equivalent thickness of the object to be imaged.

3. The method according to claim 1, wherein determining the characteristics of the object comprises estimating a mechanical thickness of the object to be imaged.

4. The method according to claim 1, wherein the determining the characteristics of the object to be imaged comprises determining a weight or a body mass of the patient.

5. A non-transitory computer-readable media comprising program code instructions configured to implement the method of claim 1 when said program code is executed by a computer.

6. The method according to claim 1, wherein the controlling movement of the at least one anti-diffusion grid relative to the operational position limits a need to increase an intensity of the radiation emitted by the source during imaging.

7. The method according to claim 1, wherein the determining the characteristics of the object to be imaged further comprises determining a composition of the structure to be imaged.

8. The method according to claim 1, wherein a duration of a mammography exam using the recited method requires no more time than a conventional mammography exam.

* * * * *